(12) United States Patent
Mahoney et al.

(10) Patent No.: US 10,130,648 B2
(45) Date of Patent: Nov. 20, 2018

(54) THERAPEUTIC COMPOSITION

(71) Applicant: Dermarc LLC, Wayne, PA (US)

(72) Inventors: Linda M. Mahoney, Phoenixville, PA (US); Anne T. Moore, Hatfield, PA (US); Gary Lee Feiss, Telford, PA (US); Danielle N. Ringhoff, Hellertown, PA (US)

(73) Assignee: Dermarc LLC, Wayne, PA (US)

( * ) Notice: Subject to any disclaimer, the term of this patent is extended or adjusted under 35 U.S.C. 154(b) by 0 days.

(21) Appl. No.: 15/266,165

(22) Filed: Sep. 15, 2016

(65) Prior Publication Data

US 2017/0000813 A1  Jan. 5, 2017

Related U.S. Application Data

(62) Division of application No. 15/171,646, filed on Jun. 2, 2016.

(60) Provisional application No. 62/172,463, filed on Jun. 8, 2015.

(51) Int. Cl.

| | | |
|---|---|---|
| *A61K 31/7048* | (2006.01) | |
| *A61K 47/38* | (2006.01) | |
| *A61K 47/10* | (2017.01) | |
| *A61K 31/365* | (2006.01) | |
| *A61K 9/06* | (2006.01) | |
| *A61K 9/00* | (2006.01) | |
| *A61K 47/12* | (2006.01) | |
| *A61K 31/704* | (2006.01) | |
| *A61K 31/341* | (2006.01) | |
| *A61K 45/06* | (2006.01) | |
| *A61K 31/635* | (2006.01) | |

(52) U.S. Cl.
CPC ........ *A61K 31/7048* (2013.01); *A61K 9/0014* (2013.01); *A61K 9/06* (2013.01); *A61K 31/341* (2013.01); *A61K 31/635* (2013.01); *A61K 31/704* (2013.01); *A61K 45/06* (2013.01); *A61K 47/10* (2013.01); *A61K 47/12* (2013.01); *A61K 47/38* (2013.01)

(58) Field of Classification Search
CPC .............. A61K 31/7048; A61K 31/635; A61K 31/704; A61K 47/38; A61K 47/10; A61K 47/12; A61K 9/06; A61K 9/0014
See application file for complete search history.

(56) References Cited

U.S. PATENT DOCUMENTS

| | | | |
|---|---|---|---|
| 2003/0235627 A1 | 12/2003 | Maibach et al. | |
| 2004/0043946 A1 | 3/2004 | Popp | |
| 2006/0205679 A1* | 9/2006 | Streeper | A61K 31/7048 514/26 |
| 2008/0220066 A1* | 9/2008 | Hartley | A61K 9/0014 424/486 |

OTHER PUBLICATIONS

Definition of prevent, Oxford English Dictionary Online, http://dictionary.oed.com/, accessed online Mar. 27, 2010, especially definition 9a. at p. 2.*
Lieberman et al., Pharmaceutical Dosage Forms: Disperse Systems, 1996, Informa Health Care, vol. 3, p. 207-209.*
Gennaro, A.R., ed., Remington's Pharmaceutical Sciences, 1985, Mack Publishing Company, 17th ed., p. 249-257, p. 1478-1486, and p. 1567-1584.*
Zhai et al., eds., Marzulli and Maibach's Dermatotoxicology, 2008, CRC Press, 7th ed., p. 51-61.*
Hartley, C.E., The effects of lithium and potassium on macromolecular synthesis in herpes simplex virus-infected cells, Journal of General Virology (1993), 74, 1519-1525.
International Search Report of PCT/US16/35443 dated Sep. 6, 2016.
Wilbur, R.L., The Difference Between Topical and Transdermal Medications. White Paper. Gensco Pharma. May 2017. https://genscopharma.com/difference-topical-transdermal-medications/.

* cited by examiner

*Primary Examiner* — Jonathan S Lau
(74) *Attorney, Agent, or Firm* — Caesar Rivise, PC

(57) ABSTRACT

This invention relates to a topical composition for prevention and treatment of viral infections.

7 Claims, 5 Drawing Sheets

THERAPEUTIC COMPOSITION

CROSS-REFERENCE TO RELATED APPLICATIONS

This application is a Divisional of U.S. Ser. No. 15/171,646 filed Jun. 2, 2016 which claims priority to U.S. Ser. No. 62/172,463, filed Jun. 8, 2015, which are incorporated by reference herein in their entireties.

BACKGROUND OF THE INVENTION

1. Field of Invention

This invention relates to a topical composition for prevention and treatment of viral infections.

2. Description of Related Art

The inventors have developed Ionic Contra-Viral Therapy for the treatment of HPV-related skin diseases. Ionic Contra-Viral Therapy (ICVT) was described in 2006 as a novel approach to the treatment of DNA viruses by local application of certain compounds that inhibit the transport of sodium and potassium across cellular membranes (Hartley, Ionic Contra-Viral Therapy (ICVT); a new approach to the treatment of DNA virus infections. Archives of Virology. December 2006, Volume 151, Issue 12, pp 2495-2501). The disturbances in the intracellular environment created by this inhibition are believed to compromise the ability of viruses to proliferate, as intracellular K+ is necessary for viral DNA synthesis (Hartley, The effects of lithium and potassium on macromolecular synthesis in herpes simplex virus-infected cells. Journal of General Virology (1993), 74, 1519-1525). Depletion of intracellular K+ in DNA virus-infected host cells provides a novel and effective approach to antiviral therapy. ICVT, is envisioned to have potential clinical utility in indications which are caused by or related to, for example, human papillomavirus, including cutaneous warts.

Overall, an evidence-based approach to therapy for cutaneous warts indicates that there is no single therapy that has proven effective in all (or even most) patients. This represents a significant unmet medical need for novel therapy. ICVT represents an opportunity to utilize the contra-viral activity of digoxin and/or furosemide as found in non-clinical and in vitro studies against HPV as a potentially effective treatment for, for example, cutaneous warts. The approach will utilize, for example, an initially short course of treatment, while attempting to limit the potential for systemic exposure to either drug.

All references cited are incorporated herein by reference in their entireties.

BRIEF SUMMARY OF THE INVENTION

The invention provides a pharmaceutical topical gel formulation comprising: at least one diuretic; alkylene glycol in the range of about 20-60% w/w; ethanol in the range of about 20-60% w/w; at least one thickener in the range of about 0.5% to 5% w/w; a buffer which maintains the formulation pH at about pH 3 to about pH 8; and optionally, polyalkylene glycol in the range of about 0-20% w/w; q.s. with water, wherein the concentrations are based on the total weight of the formulation, further wherein the topical gel formulation is anti-viral.

The invention provides a pharmaceutical topical gel formulation wherein the topical gel formulation is storage stable at room temperature. The invention provides a pharmaceutical topical gel formulation wherein the buffer is in the range of about 2-15% w/w. The invention provides a pharmaceutical topical gel formulation wherein the topical gel formulation is capable of cutaneous and/or dermal delivery. The invention provides a pharmaceutical topical gel formulation wherein the diuretic is selected from the group consisting of furosemide, bumetanide, ethacrynic acid, torsemide, muzolimide, azosemide, piretanide, tripamide, chlorothiazide, hydrochlorothiazide, chlorthandone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, benzothiazide, and combinations thereof.

The invention provides a pharmaceutical topical gel formulation wherein the diuretic is furosemide. The invention provides a pharmaceutical topical gel formulation wherein said diuretic is present at range of about 0.01-10 w/w %.

The invention provides a pharmaceutical topical gel formulation wherein the alkylene glycol is propylene glycol. The invention provides a pharmaceutical topical gel formulation capable of transcutaneous delivery of said diuretic through the stratum corneum to the basal epidermis. The invention provides a pharmaceutical topical gel formulation wherein said diuretic is capable of percutaneous absorption. The invention provides a pharmaceutical topical gel formulation in combination with an occlusive dressing, coating or other layer. The invention provides a pharmaceutical topical gel formulation wherein the buffer is a buffer system selected from the group consisting of citric acid and sodium citrate; citric acid and potassium citrate; phosphoric acid and sodium phosphate; phosphoric acid and potassium phosphate; amino acid bases and their acids; arginine and arginine HCl; lysine and lysine HCl; tartaric acid and sodium tartrate; tartaric acid and potassium tartrate; adipic acid and sodium adipate; adipic acid and potassium adipate; malic acid and sodium malate; malic acid and potassium malate; sodium phosphate monobasic and sodium phosphate dibasic; and combinations thereof. The invention provides a pharmaceutical topical gel formulation wherein the buffer is a buffering agent selected from the group consisting of sodium hydroxide, potassium hydroxide, and combinations thereof. The invention provides a pharmaceutical topical gel formulation wherein the buffer is citrate buffer. The invention provides a pharmaceutical topical gel formulation wherein the buffer is citric acid and sodium citrate. The invention provides a pharmaceutical topical gel formulation further comprising at least one excipient which is skin-tolerant and/or keratolytic. The invention provides a pharmaceutical topical gel formulation in which the gel carrier medium comprises a cosolvent mix. The invention provides a pharmaceutical topical gel formulation in which the pH is less than 7. The invention provides a pharmaceutical topical gel formulation in which the pH is about 6.3 to about 6.8. The invention provides a pharmaceutical topical gel formulation in which the thickener comprises one or more of the following: Carbomers, cellulose derivatives, or hydroxyalkylcellulose. The invention provides a pharmaceutical topical gel formulation wherein the thickener comprises hydroxypropylcellulose, in an amount of about 1 to 5% by weight based on the total weight of the formulation. The invention provides a pharmaceutical topical gel formulation wherein the thickener comprises hydroxypropylcellulose, in an amount of about 3% by weight based on the total weight of the formulation. The invention provides a pharmaceutical topical gel formulation comprising a thickener in an amount of 0.5 to 5% by weight, based on the total weight of the formulation. The invention provides a pharmaceutical topical gel formulation further including at least one of the following: an emulsifier, antioxidant, propellant, colour, buffer, preservative, or adhesive. The invention provides a pharmaceutical topical gel formulation for use in the treatment of conditions selected from the group consisting of DNA viral infections and RNA viral infections.

The invention provides a pharmaceutical topical gel formulation for use in the prevention and/or treatment of DNA viral infections selected from viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof. The invention provides a pharmaceutical topical gel formulation for use in the treatment of actinic keratoses. The invention provides a pharmaceutical topical gel formulation for use in the topical treatment of warts. The invention provides a pharmaceutical topical gel formulation for use in the reduction or prevention of viral replications by reduction or depletion of intracellular potassium ions. The invention provides a pharmaceutical topical gel formulation for use in the preparation of a medicament for use in treating a DNA viral infection. The invention provides a pharmaceutical topical gel formulation in which the DNA virus is human papilloma virus. The invention provides a pharmaceutical topical gel formulation for use in the preparation of a medicament for use in topical application to warts. The invention provides a pharmaceutical topical gel formulation for use in the preparation of a medicament for use in reducing or depleting intracellular potassium ions. The invention provides a pharmaceutical topical gel formulation comprising about 0.125% w/w furosemide, about 38.75% w/w ethanol, about 48.44% w/w propylene glycol, about 3.00% w/w hydroxypropylcellulose, about 9.69% w/w citrate buffer, and q.s. water.

The invention provides a method for treating or preventing a disease or condition in a patient, wherein the disease or condition is selected from the group consisting of viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof, wherein said method comprises: selecting a patient in need of treating or preventing said disease or condition; administering to the patient the composition of the invention in a therapeutically effective amount, thereby treating or preventing said disease in said patient.

The invention provides a pharmaceutical topical gel formulation comprising: at least one cardiac glycoside; alkylene glycol in the range of about 20-60% w/w; ethanol in the range of about 20-60% w/w; at least one thickener in the range of about 0.5% to 5% w/w; a buffer which maintains the formulation pH at about pH 3 to about pH 8; and optionally, polyalkylene glycol in the range of about 0-20% w/w; q.s. with water, wherein the concentrations are based on the total weight of the formulation, further wherein the topical gel formulation is anti-viral.

The invention provides a pharmaceutical topical gel formulation wherein the topical gel formulation is storage stable at room temperature. The invention provides a pharmaceutical topical gel formulation wherein the buffer is in the range of about 2-15% w/w. The invention provides a pharmaceutical topical gel formulation wherein the topical gel formulation is capable of cutaneous and/or dermal delivery. The invention provides a pharmaceutical topical gel formulation wherein the cardiac glycoside comprises one or more of the following: digoxin, digitoxin, methyl digoxin, lanatoside C, proscillaridin, k strophantin, peruvoside and ouabain. The invention provides a pharmaceutical topical gel formulation wherein the cardiac glycoside is digoxin. The invention provides a pharmaceutical topical gel formulation wherein said cardiac glycoside is present at range of about 0.01-10 w/w %.

The invention provides a pharmaceutical topical gel formulation wherein the alkylene glycol is propylene glycol. The invention provides a pharmaceutical topical gel formulation, capable of transcutaneous delivery of said glycoside through the stratum corneum to the basal epidermis. The invention provides a pharmaceutical topical gel formulation wherein said glycoside is capable of percutaneous absorption. The invention provides a pharmaceutical topical gel formulation in combination with an occlusive dressing, coating or other layer. The invention provides a pharmaceutical topical gel formulation wherein the buffer is a buffer system selected from the group consisting of citric acid and sodium citrate; citric acid and potassium citrate; phosphoric acid and sodium phosphate; phosphoric acid and potassium phosphate; amino acid bases and their acids; arginine and arginine HCl; lysine and lysine HCl; tartaric acid and sodium tartrate; tartaric acid and potassium tartrate; adipic acid and sodium adipate; adipic acid and potassium adipate; malic acid and sodium malate; malic acid and potassium malate; sodium phosphate monobasic and sodium phosphate dibasic; and combinations thereof. The invention provides a pharmaceutical topical gel formulation wherein the buffer is a buffering agent selected from the group consisting of sodium hydroxide, potassium hydroxide, and combinations thereof. The invention provides a pharmaceutical topical gel formulation wherein the buffer is citrate buffer. The invention provides a pharmaceutical topical gel formulation wherein the buffer is citric acid and sodium citrate. The invention provides a pharmaceutical topical gel formulation further comprising at least one excipient which is skin-tolerant and/or keratolytic. The invention provides a pharmaceutical topical gel formulation, in which the gel carrier medium comprises a cosolvent mix. The invention provides a pharmaceutical topical gel formulation in which the pH is less than 7. The invention provides a pharmaceutical topical gel formulation in which the pH is about 6.3 to about 6.8. The invention provides a pharmaceutical topical gel formulation in which the thickener comprises one or more of the following: Carbomers, cellulose derivatives, or hydroxyalkylcellulose. The invention provides a pharmaceutical topical gel formulation wherein the thickener comprises hydroxypropylcellulose, in an amount of about 1 to 5% by weight based on the total weight of the formulation. The invention provides a pharmaceutical topical gel formulation wherein the thickener comprises hydroxypropylcellulose, in an amount of about 3% by weight based on the total weight of the formulation. The invention provides a pharmaceutical topical gel formulation comprising a thickener in an amount of 0.5 to 5% by weight, based on the total weight of the formulation.

The invention provides a pharmaceutical topical gel formulation further including at least one of the following: an emulsifier, antioxidant, propellant, colour, buffer, preservative, or adhesive. The invention provides a pharmaceutical topical gel formulation for use in the treatment of conditions selected from the group consisting of DNA viral infections and RNA viral infections. The invention provides a pharmaceutical topical gel formulation for use in the prevention and/or treatment of DNA viral infections selected from viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof. The invention provides a pharmaceutical topical gel formulation for use in the treatment of actinic keratoses. The invention provides a pharmaceutical topical gel formulation for use in the topical treatment of warts. The invention provides a pharmaceutical topical gel formulation for use in the reduction or prevention of viral replications by reduction or depletion of intracellular potassium ions. The invention provides a pharmaceutical topical gel formulation for use in the preparation of a medicament for use in treating a DNA viral infection. The invention provides a pharmaceutical topical gel formulation in which the DNA virus is human papilloma virus. The invention provides a pharmaceutical topical gel formulation for use in the preparation of a medicament for use in topical application to warts. The invention provides a pharmaceutical topical gel formulation, for use in the preparation of a medicament for use in reducing or depleting intracellular potassium ions. The invention provides a pharmaceutical topical gel formulation comprising about 0.125% w/w digoxin, about 38.75% w/w ethanol, about 48.44% w/w propylene glycol, about 3.00% w/w hydroxypropylcellulose, about 9.69% w/w citrate buffer, and q.s. water.

The invention provides a method for treating or preventing a disease or condition in a patient, wherein the disease or condition is selected from the group consisting of viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof, wherein said method comprises: selecting a patient in need of treating or preventing said disease or condition; administering to the patient the composition of the invention in a therapeutically effective amount, thereby treating or preventing said disease in said patient.

The invention provides a pharmaceutical topical gel formulation comprising: at least one diuretic; at least one cardiac glycoside; alkylene glycol in the range of about 20-60% w/w; ethanol in the range of about 20-60% w/w; at least one thickener in the range of about 0.5% to 5% w/w; a buffer which maintains the formulation pH at about pH 3 to about pH 8; and optionally, polyalkylene glycol in the range of about 0-20% w/w; q.s. with water, wherein the concentrations are based on the total weight of the formulation further wherein the topical gel formulation is antiviral.

The invention provides a pharmaceutical topical gel formulation wherein the topical gel formulation is stable at room temperature. The invention provides a pharmaceutical topical gel formulation wherein the buffer is in the range of about 2-15% w/w.

The invention provides a pharmaceutical topical gel formulation wherein the topical gel formulation is capable of cutaneous and/or dermal delivery. The invention provides a pharmaceutical topical gel formulation wherein the cardiac glycoside is digoxin. The invention provides a pharmaceutical topical gel formulation wherein the diuretic is selected from the group consisting of furosemide, bumetanide, ethacrynic acid, torsemide, muzolimide, azosemide, piretanide, tripamide, chlorothiazide, hydrochlorothiazide, chlorthandone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, benzothiazide, and combinations thereof. The invention provides a pharmaceutical topical gel formulation wherein at least one loop diuretic is present in combination with at least one cardiac glycoside. The invention provides a pharmaceutical topical gel formulation wherein the cardiac glycoside comprises one or more of the following: digoxin, digitoxin, methyl digoxin, lanatoside C, proscillaridin, k strophantin, peruvoside and ouabain. The invention provides a pharmaceutical topical gel formulation wherein said diuretic is present at range of about 0.01-10 w/w %. The invention provides a pharmaceutical topical gel formulation wherein said cardiac glycoside is present at range of about 0.01-10 w/w %. The invention provides a pharmaceutical topical gel formulation wherein a molar ratio of cardiac glycoside:loop diuretic is in the range of about 0.5 to 2.5:20 to 0.5.

The invention provides a pharmaceutical topical gel formulation wherein the buffer is a buffer system selected from the group consisting of citric acid and sodium citrate; citric acid and potassium citrate; phosphoric acid and sodium phosphate; phosphoric acid and potassium phosphate; amino acid bases and their acids; arginine and arginine HCl; lysine and lysine HCl; tartaric acid and sodium tartrate; tartaric acid and potassium tartrate; adipic acid and sodium adipate; adipic acid and potassium adipate; malic acid and sodium malate, malic acid and potassium malate; sodium phosphate monobasic and sodium phosphate dibasic; and combinations thereof. The invention provides a pharmaceutical topical gel formulation wherein the buffer is a buffering agent selected from the group consisting of sodium hydroxide, potassium hydroxide, and combinations thereof. The invention provides a pharmaceutical topical gel formulation wherein the buffer is citrate buffer. The invention provides a pharmaceutical topical gel formulation wherein the pH is less than 7. The invention provides a pharmaceutical topical gel formulation in which the pH is about 6.5 to about 6.8. The invention provides a pharmaceutical topical gel formulation in which the pH is about 5.5.

The invention provides a pharmaceutical topical gel formulation in which the thickener comprises one or more of the following: Carbomers, cellulose derivatives, hydroxyalkylcelluloses, or hydroxypropylcellulose. The invention provides a pharmaceutical topical gel formulation wherein the thickener comprises hydroxypropylcellulose, in an amount of about 1 to about 5% by weight based on the total weight of the formulation. The invention provides a pharmaceutical topical gel formulation wherein the thickener comprises hydroxypropylcellulose, in an amount of about 3% by weight based on the total weight of the formulation. The invention provides a pharmaceutical topical gel formulation further comprising at least one excipient which is skin-tolerant and/or keratolytic. The invention provides a pharmaceutical topical gel formulation comprising about 0.125% w/w digoxin, about 0.125% w/w furosemide, about 38.70% w/w ethanol, about 48.38% w/w propylene glycol, about 3.00% w/w hydroxypropylcellulose, about 9.68% w/w citrate buffer, and q.s. water. The invention provides a pharmaceutical topical gel formulation for use in the prevention and/or treatment of conditions selected from the group consisting of viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof. The invention provides a pharmaceutical topical gel formulation for use in the topical treatment of warts. The invention provides a pharmaceutical topical gel formulation for use in the reduction or prevention of viral replications by reduction or depletion of intracellular potassium ions.

The invention provides a pharmaceutical topical gel formulation for use in the preparation of a medicament for use in treating a DNA virus. The invention provides a pharmaceutical topical gel formulation in which the DNA virus is human papilloma virus. The invention provides a pharmaceutical topical gel formulation for use in the preparation of a medicament for use in topical application to warts. The invention provides a pharmaceutical topical gel formulation for use in the preparation of a medicament for use in reducing or depleting intracellular potassium ions.

A method for treating or preventing a disease or condition in a patient, wherein the disease or condition is selected from the group consisting of viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof, wherein said method comprises: selecting a patient in need of treating or preventing said disease or condition; administering to the patient the composition of the invention in a therapeutically effective amount, thereby treating or preventing said disease in said patient.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
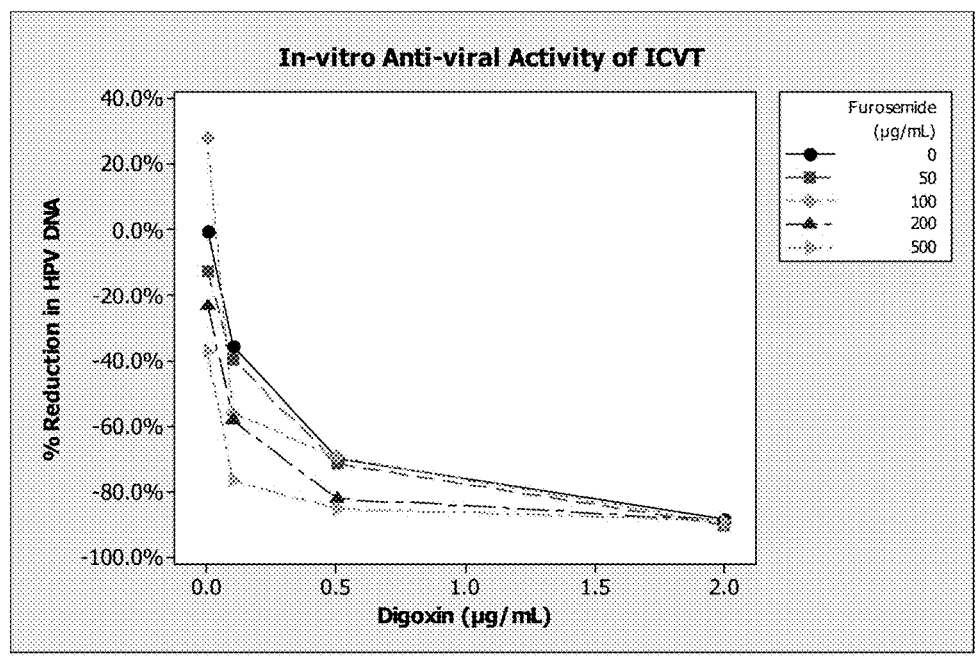
FIG. 1 shows the In-vitro anti-viral activity of Ionic Contra-Viral Therapy; Summary of in vitro efficacy against HPV18 in Hela cell culture; % Reduction in HPV DNA. Single and combined drug 48 hour treatment experiment.

The invention is directed to the use of, for example, a topical formulation, for treating or preventing viral infections.

As used herein, the term "effective amount" refers to the amount of a therapy that is sufficient to result in the prevention of the development, recurrence, or onset of a disease or condition, such as neoplasia or infection, and one or more symptoms thereof, to enhance or improve the prophylactic effect(s) of another therapy, reduce the severity, the duration of a disease or condition, such as neoplasia or infection, ameliorate one or more symptoms of a disease or condition such as warts or HPV infection, prevent the advancement or recurrence of a disease or condition, such as warts or HPV infection, cause regression of a disease or condition, such as warts or HPV infection, and/or enhance or improve the therapeutic effect(s) of another therapy.

By "pharmaceutically acceptable," such as in the recitation of a "pharmaceutically acceptable carrier," or a "pharmaceutically acceptable derivative," is meant a compound that is not biologically or otherwise undesirable, i.e., the compound may be incorporated into a topical formulation of the invention and administered to a patient without causing any undesirable biological effects or interacting in a deleterious manner with any of the other components of the formulation in which it is contained. A "pharmacologically active" compound refers to an active agent as defined above, or to an analog or derivative thereof having the same type of pharmacological activity as the parent compound. As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, such as warts or HPV infection, or a symptom thereof in a subject resulting from the administration of a therapy (e.g., a prophylactic or therapeutic agent), or a combination of therapies (e.g., a combination of prophylactic or therapeutic agents).

As used herein, the terms "subject" and "patient" are used interchangeably. As used herein, the term "patient" refers to an animal, preferably a mammal such as a non-primate (e.g., cows, pigs, horses, cats, dogs, rats, etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the terms "therapies" and "therapy" can refer to any method(s), composition(s), and/or agent(s) that can be used in the prevention, treatment and/or management of a disease or condition, such as neoplasia or infection, or one or more symptoms thereof.

As used herein, the terms "treat," "treatment," and "treating" in the context of the administration of a therapy to a subject refer to the reduction or inhibition of the progression and/or duration of a disease or condition, such as warts or HPV infection, the reduction or amelioration of the severity of a disease or condition, such as neoplasia or infection, and/or the amelioration of one or more symptoms thereof resulting from the administration of one or more therapies. The terms "treating" and "treatment" as used herein refer to actions that reduce the severity and/or frequency of symptoms, eliminate symptoms and/or their underlying cause, prevent the occurrence of symptoms and/or their underlying cause, and improve or remediate damage. The present method of "treating" a patient, as the term is used herein, thus encompasses both prevention of warts in a predisposed individual and treatment of warts in a clinically symptomatic individual.

The term "topical administration" is used in its conventional sense to mean delivery of a topical drug or pharmacologically active agent to the skin or mucosal tissue, as in, for example, the treatment of warts.

As used herein the term "papillomavirus disease" refers to any kind of infection or disorder caused by the virus, including cancers and warts. Thus, the term includes symptoms and side effect of any papillomavirus infection, including latent, persistent and sub-clinical infections, whether or not the infection is clinically apparent.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As referred to herein the term "storage stable" and/or "storage stability" means stable for greater than 18 months at room temperature, wherein stable is defined as maintaining ≥90% of the targeted active concentration. Stable may also refer to a degradation profile limited to low levels (<5% degradation) and no toxic degradants.

Human Papillomavirus

Human papillomavirus (HPV) refers to a group of DNA tumor viruses that can induce neoplastic proliferation of human epithelial cells. There are currently over 130 documented strains of HPV and many more are being identified. The current classification system, which is based on similarities in genomic sequences, generally correlates with the 3 clinical categories applied to HPV: anogenital or mucosal, nongenital cutaneous, and epidermodysplasia verruciformis (EV). Mucosal HPV infections are further classified as latent (asymptomatic), subclinical, and clinical.

Clinical lesions are grossly apparent, whereas latent infections are detected only with tests for viral DNA. Subclinical lesions are identified by application of 3-5% acetic acid and inspection under magnification. Most HPV infections are latent; clinically apparent infections usually result in warts rather than malignancies. However, infections due to HPV are common and lead to a wide variety of clinical manifestations; certain types of HVP (6, 11, 16, and 18) can place patients at a high risk for anogenital cancer. HPVs 5, 8, 15, 20, 24, and 26 are associated with actinic keratosis and development of squamous cell carcinoma. HPVs 16 and 18 are classified as high risk for cervical cancer. The HPV genotypes associated with various diseases are presented in the following tables (source emedicine.medscape.com/article/219110-overview).

| Nongenital Cutaneous Disease | HPV Type |
| --- | --- |
| Common warts (verrucae vulgaris) | 1, 2, 4, 26, 27, 29, 41, 57, 65, 75-78 |
| Plantar warts (myrmecias) | 1, 2, 4, 60, 63 |
| Flat warts (verrucae planae) | 3, 10, 27, 28, 38, 41, 49 |
| Butcher's warts (common warts of people who handle meat, poultry, and fish) | 1-4, 7, 10, 28 |
| Mosaic warts | 2, 27, 57 |
| Ungual squamous cell carcinoma | 16 |
| Epidermodysplasia verruciformis (benign) | 2, 3, 10, 12, 15,19, 36, 46, 47, 50 |
| Epidermodysplasia verruciformis (malignant or benign) | 5, 8-10, 14, 17, 20-25, 37, 38 |
| Nonwarty skin lesions | 37, 38 |

| Nongenital Mucosal Disease | HPV Type |
| --- | --- |
| Respiratory papillomatosis | 6, 11 |
| Squamous cell carcinoma of the lung | 6, 11, 16, 18 |
| Laryngeal papilloma (recurrent respiratory papillomatosis) | 2, 6, 11, 16, 30, 40, 57 |
| Laryngeal carcinoma | 6, 11 |
| Maxillary sinus papilloma | 57 |
| Squamous cell carcinoma of the sinuses | 16, 18 |
| Conjunctival papillomas | 6, 11 |
| Conjunctival carcinoma | 16 |
| Oral focal epithelial hyperplasia (Heck disease) | 13, 32 |
| Oral carcinoma | 16, 18 |
| Oral leukoplakia | 16, 18 |
| Squamous cell carcinoma of the esophagus | 16, 18 |

| Anogenital Disease | HPV Type |
| --- | --- |
| Condylomata acuminata | 1-6, 10, 11, 16, 18, 30, 31, 33, 35, 39-45, 51-59, 70, 83 |
| Bowenoid papulosis | 16, 18, 34, 39, 40, 42, 45 |
| Bowen disease | 16, 18, 31, 34 |
| Giant condylomata (Buschke-Löwenstein tumors) | 6, 11, 57, 72, 73 |
| Unspecified intraepithelial neoplasia | 30, 34, 39, 40, 53, 57, 59, 61, 62, 64, 66-69 |
| Low-grade squamous intraepithelial lesions (LGSIL) | 6, 11, 16, 18, 26, 27, 30, 31, 33-35, 40, 42-45, 51-58, 61, 62, 67-69, 71-74, 79, 81-84 |
| High-grade squamous intraepithelial lesions (HGSIL) | 6, 11, 16, 18, 31, 33, 35, 39, 42, 44, 45, 51, 52, 56, 58, 61, 64, 66, 68, 82 |
| Carcinoma of vulva | 6, 11, 16, 18 |
| Carcinoma of vagina | 16 |
| Carcinoma of cervix | 16, 18, 31, 33, 35, 39, 45, 51, 52, 56, 58, 59, 66, 68, 70, 73, 82 |
| Carcinoma of anus | 16, 31, 32, 33 |
| Carcinoma of in situ of penis erythroplasia of Queyrat) | 16 |
| Carcinoma of | 16, 18 |

HPV is spread via skin or fomite surface contact. Infection via the environment is more likely to occur if the skin is macerated and in contact with roughened surfaces—conditions which are common in swimming pools and communal washing areas (Sterling, 2001). There are very few precise epidemiological data on viral warts. Most prevalence surveys have tended to use selected subsets of the population such as dermatology outpatients or school children. In the general population, viral warts are uncommon in infancy, increasingly common in childhood (reaching a peak in the teenage years) and sharply declining in prevalence thereafter (Gibbs, 2009).

Human Papillomavirus and Cutaneous Warts

Cutaneous wart diagnosis is generally based on clinical examination, but can be suggested by histological appearances of epidermis with papillomatosis, hyperkaratosis, and parakeratosis. Dermal capillary vessels may be prominent and thrombosed. There may be large keratinocytes with eccentric pyknotic nuclei surrounded by a perinuclear halo. HPV-infected cells can have small eosinophilic granules and diffuse clumps of basophilic keratohyline granules—these are not HPV particles. Plantar warts must be distinguished from callosities and corns. Flat warts have less acanthosis and hyperkeratosis and do not have parakeratosis or papillomatosis.

A published report in March 2012 examined the prevalence of cutaneous wart-associated HPV types and their relation with patient characteristics. Samples were taken from 250 patients, age range 4 to 50 years that had one or more new cutaneous warts. HPV 27, 57, 2 and 1 were the most prevalent types; in only 14% of warts were other HPV types detected. In 74% of patients with multiple warts, one HPV type was shared in all warts of that patient. It is suggested that a co-infection of single cells with multiple HPV types could be responsible for the development of some warts with multiple types. If specific HPV infections prove to be associated with clearance or response to specific treatment, HPV genotyping or HPV type assessment based on clinical profiles may become relevant for daily practice (Bruggink, 2012).

Diseases which may be prevented and/or treated by the processes and compositions of this invention are those caused by the etiological agent, papillomavirus, and may be the result of clinical or sub-clinical PV infections. Such diseases include, for example, epithelial malignancies, anogenital malignancies, such as cervical cancer, malignant lesions, benign lesions, papillomacarcinomas, papilloadenocystomas, papilloma neurophathicum, papillomatosis, cutaneous and mucosal papillomas, condylomas, oral, pharyngeal, laryngeal, and tongue papillomas, fibroblastic tumors and other pathological conditions associated with papillomavirus. The composition of this invention may also be used to treat epithelial and internal fibropapillomas in animals.

In addition, as described above, a wide variety of warts are found on human skin and are caused by the human papillomavirus (HPV). For example, the following types of warts are found on human skin and are caused by the human papillomavirus (HPV): common warts (verruca vulgaris), plantar warts, palmar warts, planar warts (verruca plana), mosaic warts, and venereal warts (condyloma accuminatum). These skin growths are unsightly, irritating, and potentially oncogenic (carcinogenic), and their removal is desired.

Genital warts, also referred to as venereal warts and condylomata acuminata, are one of the most serious manifestations of HPV infection. As reported by the Center for Disease Control, the sexual mode of transmission of genital warts is well established and the incidence of genital warts is on the increase. The seriousness of genital warts is underlined by the finding that HPV DNA can be found in all grades of cervical intraepithelial neoplasia (CIN I III) and that a specific subset of HPV types can be found in carcinoma in situ of the cervix. In addition, VIN (vulvar intraepithelial neoplasia) is associated with HPV and is considered a pre-cancerous condition. Consequently, women with genital warts, containing specific HPV types are now considered at high risk for the development of cervical cancer. Current treatments for genital warts are inadequate. According to the present invention, a method of treating a patient having one or more genital warts comprises the administration of a pharmaceutical of the invention so as to inhibit growth of the wart. In preferred embodiments, the wart(s), or other PV-containing cells, are contacted directly with the pharmaceutical composition. The subject method can be used to treat, e.g., condyloma acuminata and/or flat cervical warts.

Laryngeal papillomas are benign epithelial tumors of the larynx. Two PV types, HPV-6 and HPV-11, are most commonly associated with laryngeal papillomas. According to the method of the present invention, laryngeal papillomas are treated administrating a pharmaceutical composition of the invention, so as to inhibit growth of the papillomas.

The most common disease associated with papillomavirus infection are benign skin warts. Common warts generally contain HPV types 1, 2, 3, 4 or 10. These warts typically occur on the soles of feet, plantar warts, or on the hands. Common skin warts are most often found in children and young adults. Later in life the incidence of common warts decreases presumably due to immunologic and physiologic changes. Plantar warts can often be debilitating and require surgical removal and they frequently reoccur after surgery. As above, patients suffering from common warts can be treated by the administration of a effective amount of an E2 peptidomimetic according to the present invention, or a gene therapy construct which encodes the therapeutic E2 peptide. In preferred embodiments, the peptide or gene construct are applied, in the appropriate formulations, directly to the area of the skin afflicted with the wart(s). Similar methods and compositions may be useful in the treatment if epidermodysplasia verruciformis (EV), a rare genetically transmitted disease which is characterized by disseminated flat warts that appear as small reddish macules.

In addition, the subject method and compositions may be used to treat lesions resulting from cellular transformation for which HPV is a etiological agent, e.g., in the treatment of cervical cancer.

In some cases, HPV may cause epidermodysplasia verruciformis in immunocompromised individuals. There is currently no specific treatment for HPV infection.

Other DNA Viruses

In one aspect, the method of the present invention can be used to treat viral infection in an individual caused by human papillomavirus (HPV), human T-lymphotropic virus type I (HTLV-1), herpes virus (e.g., EBV or CMV), SV40-like virus, hepatitis virus, human immunodeficiency virus (HIV), adenovirus, or influenza virus. The present method can also be used to treat infections caused by other viruses that are responsive to treatment by artemisinin or artemisinin derivatives, such as DNA viruses and RNA viruses. Such viruses may or may not cause cancer.

Herpes simplex virus (HSV) is a double stranded DNA virus and can enter into target organisms through the mouth, respiratory passage, genital tract mucosa, damaged skin and many other channels. It is a quite common infection among humans and the infection rate is as high as 80-90%. Typical symptoms include clusters of blisters on certain parts of the mucosa and skin, while occasionally serious systemic disease may occur and do harm to the internal organs. Previous researches indicated that HSV-1 and HSV-2 might separately be related to lip cancer, vulva cancer and cervix cancer and lots of attentions have been drawn to them (Sunhe, China practical gynaecology and obstetrics journal, 2001, 17 (7):407-409). Presently, drugs for treating HSV infection include idoxuridine, cytosine arabino side, vidarabine, bromovinyl, uridine, acyclovir and so on. But the treatment time of these drugs are quite long, about 5-7 days.

Another example of a viral-induced skin lesion are the lesions caused by Molluscum contagiosum (MC). MC virus is a member of the poxvirus group. It is a large double stranded DNA virus that replicates in the cytoplasm of infected cells. Skin lesions caused by MC have an incidence of approximately 1/200 children by the age of 10 in the United States. While the disease may be epidemic in children, it occurs in people of all ages and is worldwide in distribution. In adults, the infection may be spread by sexual contact. Skin lesions caused by MC are characterized by the appearance on the body surface of small, discreet, lobulated epidermal outgrowths or lesions that occur throughout the body. These lesions, which are the result of excessive cellular proliferation stimulated in the keratinocyte layer by virus that has entered through the skin, are discrete pearly white or flesh colored papules that may persist for up to three years. The lesions may have a central pore, which contains within its center dead skin cells and numerous virus particles.

Infections caused by MC commonly last for 9-18 months but the condition can, in certain cases, persist for as long as 3-4 years. During this time, new crops of lesions appear, each lesion growing slowly for 6-12 weeks and persisting for an average of 3-4 months.

At present, there is no drug treatment for MC; the virus is resistant to the commonly used anti-viral agents which are effective in treating other viral infections and the disease is treated only by surgical removal of the lesions, e.g., cryotherapy, or tissue destruction by chemical or physical means. This can be painful and distressing, particularly for children, and does not prevent the reappearance of fresh lesions.

Cardiac Glycosides

The compositions described herein typically comprise at least one cardiac glycoside. The cardiac glycoside compositions may comprise other compounds as well. For example, the cardiac glycoside may comprise a mixture of cardiac glycosides, a mixture of a cardiac glycoside and one or more pharmaceutically acceptable excipients, or a mixture of a cardiac glycoside with other compounds having useful or desirable properties. In an exemplary embodiment, the composition of the invention may comprise at least one cardiac glycoside and at least one diuretic. In a further exemplary embodiment, the cardiac glycoside composition of the invention may comprise a cardiac glycoside as the only active agent. In an exemplary embodiment, the cardiac glycoside is digoxin. In an exemplary embodiment, the composition of the invention may comprise at least one cardiac glycoside and at least one other active agent.

Digoxin, also known as digitalis, is a purified cardiac glycoside extracted from the foxglove plant, Digitalis lanata. The systematic name for this compound is (3β,5β,12β)-3-[(O-2,6-dideoxy-β-D-ribo-hexopyranosyl-(1→4)-O-2,6-dideoxy-β-D-ribo-hexopyranosyl-(1→4)-2,6 dideoxy-B D-ribo-hexopyranosyl)oxy]-12,14-dihydroxycard-20(22)-enolide, CAS No. 20830-75-5

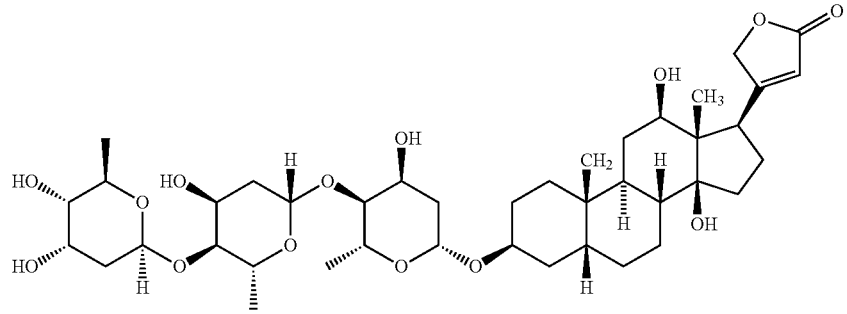

30

Molecular Formula: $C_{41}H_{64}O_{14}$, Molecular Weight: 780.94 Description: white or almost white powder or colorless crystals (PhEur) Optical Rotation: [α]D 20+13.9° to +15.9° (in methylene chloride/methanol) [α]D 20+10.0° to +13.0° (in pyridine), Melting range: 230-265° C. (under decomposition), Hygroscopicity: is not hygroscopic. Solubility: soluble in methylene chloride/methanol (1:1); practically insoluble in water; slightly soluble in ethanol (95) and freely soluble in pyridine. Digoxin preparations are commonly marketed under the trade names: Lanoxin, Digitek, and Lanoxicaps.

Digitoxin is a cardiac glycoside which is the corresponding aglycone of digoxin. Thus, it has the systematic name: (3β,5β)-3-[(O-2,6-dideoxy-β-D-ribo-hexapyranosyl-(1→4)-2,6-dideoxy-β-D-ribo-hexopyranosyl)oxy]-14-hydroxycard-20(22)-enolide. Methyl digoxin is a cardiac glycoside related to digoxin and digitoxin with the systematic name: (3β,5β,12β)-3-{[2,6-dideoxy-4-O-methyl-β-D-ribo-hexopyranosyl-(1→4)-2,6-dideoxy-β-D-ribo-hexopyranosyl-(1→4)-2,6-dideoxy-β-D-ribo-hexopyranosyl]oxy}-12,14-dihydroxycard-20(22)-enolide. Lanatoside C is a cardiac glycoside with the systematic name: [(3β,5β,12β)-3-{[(β-D-Glucopyranosyl-(1→4)-3-O-acetyl-2,6-dideoxy-β-D-ribo-hexopyranosyl-(1→4)-2,6-dideoxy-β-D-ribo-hexopyranosyl-(1→4)-2,6-dideoxy-β-D-ribo-hexopyranosyl]oxy}-12,14-dihydroxycard-20(22)-enolide [0058] Proscillaridin is a bufanolide cardiac glycoside obtainable from plants of the genus Scilla. The systematic name of this compound is: 3β-Rhamnosido-14β-hydroxybufa 4, 20, 22 trienolide. K-strophanthin refers to a cardiac glycoside or mixture of glycosides obtained from a tropical plant (Strophanthus kombe) of the dogbane family. Peruvoside refers to a cardiac glycoside with the systematic name: (3β,5β)-3-[(6-Deoxy-3-O-methyl-α-L-glucopyranosyl)oxy]-14-hydroxy-19-oxo-card-20(22)-enolide Ouabain, also known as g-strophanthin, is a cardiac glycoside found in the ripe seeds of the African plants *Strophanthus gratus* and *Acokanthera ouabaio*. The systematic name of this compound is: 1β,3β,5β,11α,14,19-Hexahydroxycard-20(22)-enolide 3-(6-deoxy-α-L-mannopyranoside). Other embodiments of cardiac glycosides include oleander and extracts and isolates thereof.

The term "cardiac glycoside" refers to a class of pharmacological agents including those that have been used to treat congestive heart failure and heart arrhythmias by inhibiting the Na+/K+ pump in cells. Inhibition of the Na+/K+ pump by cardiac glycosides leads to increased Na+ levels, which in turn slows down the extrusion of $Ca^{+2}$ via the $Na^+/Ca^{+2}$ exchange pump. Many cardiac glycosides are natural products which share a common molecular motif comprising a steroid nucleus containing an unsaturated lactone ring at the $C_{17}$ position and one or more glycosidic residues at $C_3$. Examples of cardiac glycosides include, but are not limited to, ouabain, oleandrin, g/k/e-strophanthin, digoxin, digitoxin, proscillaridine A, which are plant derived, and bufalin, marinobufagenin and bufadienolides, which are derived from frog poisons. Cardiac glycosides comprise two structural features, a sugar (glycoside) and a non-sugar (aglycone) steroid moiety.

In exemplary embodiments, the pharmaceutical composition of the invention may comprise about 0.125%, about 0.250%, about 0.50%, about 0.75%, about 1%, about 2%, about 3%, about 4%, about 5%, about 6%, about 7%, about 8%, about 9%, or about 10% w/w of the cardiac glycoside. In exemplary embodiments, the pharmaceutical composition of the invention may comprise about 0.125% to about 10%, about 0.125% to about 5%, or about 0.125% to about 3% w/w of the cardiac glycoside.

Diuretic Compounds

The compositions described herein typically comprise at least one diuretic compound. The diuretic compositions may comprise other compounds as well. For example, the diuretic composition may comprise a mixture of diuretic compounds, a mixture of a diuretic compound and a pharmaceutically acceptable excipient, or a mixture of a diuretic compound with other compounds having useful or desirable properties. In an exemplary embodiment, the composition of the invention may comprise at least one cardiac glycoside and at least one diuretic. In a further exemplary embodiment, the diuretic composition may comprise a pure diuretic compound as the only active agent. In an exemplary embodiment, the composition of the invention may comprise at least one cardiac glycoside and at least one other active agent. In an exemplary embodiment, the diuretic is furosemide: 4-Chloro-2-[(furan-2-ylmethyl)amino]-5-sulphamoylbenzoic acid (Ph. Eur.) Chemical Abstracts Service (CAS) registry number CAS 54-31-9:

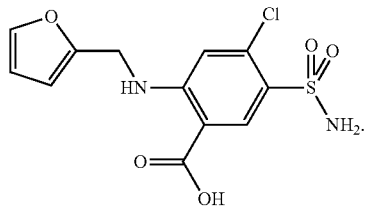 [SMILES: NS(=O)(=O)c1cc(C(=O)O)c(NCc2ccco2)cc1Cl]

Furosemide occurs as a white or almost white crystalline powder. It is practically insoluble in water; sparingly soluble in ethanol (96%); soluble in acetone and dilute alkali solutions. Furosemide has a melting point of approximately 210° C. with decomposition. Furosemide is known to have several polymorphic forms. They can be differentiated by means of X-ray diffraction patterns. The applied manufacturing process leads to the (commercial) polymorphic form I, which is the thermodynamically stable modification. Furosemide has no chiral center. The pKa value for Furosemide was found to be 3.9.

In addition, any suitable diuretic compound may be used. Classes of diuretics suitable for use with the described methods and formulations include the carbonic anhydrase inhibitors, osmotic diuretics, loop diuretics, thiazide and thiazide-like diuretics, potassium sparing diuretics, and aldosterone antagonists. Exemplary diuretic compounds within these classes include bumetanide, ethacrynic acid, furosemide, muzolimine, spironolactone, torsemide, triamterene, tripamide, BG 9928 (Bicyclo[2,2,2]octane-1-propanoic acid, 4-(2,3,6,7-tetrahydro-2,6-dioxo-1,3-dipropyl-1H-purin-8yl)-(9CI)), and BG 9719 (1H-Purine-2,6-dione, 3,7-dihydro-8-(3-oxatricyclo[3,2,1,02,4]oct-6-yl)-1,3-dipropyl-[1S-(1α,2β,4β,5α,6β)], and pharmaceutically acceptable analogs and equivalents thereof. In other specific embodiments, the diuretic is selected from the group consisting of high-ceiling diuretics, furosemide, bumetanide, ethacrynic acid, torsemide, muzolimide, azosemide, piretanide, tripamide, chlorothiazide, hydrochlorothiazide, chlorthandone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide and benzothiazide.

In exemplary embodiments, the pharmaceutical composition of the invention may comprise about 0.01%, about 0.125%, about 0.250%, about 0.50%, about 0.75%, about 1%, about 2%, about 3%, about 4%, about 5%, about 6%, about 7%, about 8%, about 9%, or about 10% w/w of the diuretic. In exemplary embodiments, the pharmaceutical composition of the invention may comprise about 0.01% to about 10%, about 0.125% to about 10%, about 0.125% to about 5%, or about 0.125% to about 3% w/w of the diuretic.

Buffering Agents

The normal pH of the skin is between about 4 and about 6.5, though it varies in people of different skin types. The compositions of the invention, therefore, in certain embodiments, may be formulated in such a manner so as to reduce the effects that the actual application of the composition has on the pH barrier of the skin and/or may be formulated in a manner so as to increase the penetration of the active agent. Accordingly, in certain embodiments the typical pH ranges for the compositions of the invention include a pH of about 3 to about 8, of about 4 to about 7, and more typically about 4.5 to about 6.5 or about 5.5. The desired pH ranges of the compositions of the invention can be obtained in accordance with practices well known in the art, for instance, by the inclusion of various buffering agents, which should be included in an amount and concentration to optimize the flux of the active agent through the skin surface and into the dermal layer of skin, while minimizing any possibility of skin irritation due to a change in the pH of the skin.

A conventional buffering agent such as a mixture of citric acid and trisodium citrate, may be added to stabilize the desired pH. Other buffering agents include, but are not limited to, sodium phosphate, monosodium dihydrogen phosphate, and disodium monohydrogen phosphate.

A citrate buffer for use in the present invention may be generated by dissolution of free citric acid or preferably a pharmaceutically acceptable salt of citrate, preferably a sodium salt. In preferred embodiments of the present invention citrate buffer is present in the formulation at 7.5 mmol/l to 15 mmol/l and most preferably at 10 mmol/l. Any pharmaceutically acceptable citrate buffer may be used in the present invention but the citrate buffer is preferably sodium citrate. It is more preferable that sodium citrate dihydrate is used and most preferable that the citrate buffer be generated from a mixture of sodium citrate dihydrate and citric acid monohydrate. In the preferred embodiments of the present invention, the formulation contains about 2 mg/ml sodium citrate dihydrate and about 0.6 mg/ml citric acid monohydrate.

A citrate buffer for use in the present invention may be generated by dissolution of free citric acid or preferably a pharmaceutically acceptable salt of citrate, preferably a sodium salt.

A formulation of the present invention may be generated by adding an amount of citrate buffer necessary to obtain a pH of the solution in the range 5.3 to 7.2. The citrate buffer is preferably present at 5 mmol/l to 20 mmol/l.

The desired pH range is from about pH 4.0 to pH 5.5. These buffering systems can be comprised of a weak acid and the salt of a weak acid and/or a mixture of two acid salts. Suitable buffering systems include, for example, citric acid and sodium citrate; citric acid and potassium citrate; phosphoric acid and sodium phosphate; phosphoric acid and potassium phosphate; amino acid bases and their acids; arginine and arginine HCl; lysine and lysine HCl; tartaric acid and sodium tartrate; tartaric acid and potassium tartrate; adipic acid and sodium adipate; adipic acid and potassium adipate; malic acid and sodium malate, malic acid and potassium malate; sodium phosphate monobasic and sodium phosphate dibasic; and combinations thereof; and the like. The buffering system should be present in an amount of from about 0.05 to 2.0%, preferably from about 0.05 to 1.0% by weight of the total composition.

The citrate buffered formulation of the invention may include an amount of citrate effective to provide a pharmaceutically acceptable pH, e.g., to provide a pH environment of between 5 and 7, preferably between about 5.3, and 6.2. In order to provide a pharmaceutically acceptable amount of citrate buffer effective to achieve the desired pH, suitable amounts of sodium citrate and citric acid can be used.

Suitable buffer systems of use in the present invention include, by way of example only, tartaric, fumaric, maleic, phosphoric, and acetic acids and salts. Preferred buffering systems include citric acid and phosphoric acid buffer systems. The citric acid buffer system preferably contains sodium citrate dihydrate USP in combination with citric acid anhydrous USP, available from Haarman & Reimer. Preferably there is about 5.1 to about 5.4 grams/liter of sodium citrate dihydrate, most preferably 5.27 grams/liter of sodium citrate dihydrate, and about 2.05 to about 2.25 grams/liter of citric acid anhydrous, preferably about 2.15 grams/liter of citric acid anhydrous. Buffering agents can also be added to the formulation to control pH.

Examples of buffering agents can be any one or more of the following agents, and is not limited to, acetic acid, ammonium carbonate, ammonium phosphate, boric acid, citric acid, glycine, lactic acid, phosphoric acid, potassium citrate, potassium metaphosphate, potassium phosphate monobasic, sodium acetate, sodium citrate, sodium hydroxide, sodium lactate solution, dibasic sodium phosphate, monobasic sodium phosphate, TRIS and sodium carbonate, 2-Amino-2-methyl-1,3-propanediol, 2-Amino-2-methyl-1-propanol, L-(+)-Tartaric acid, ACES, ADA, Acetic acid, Ammonium acetate solution, Ammonium bicarbonate, Ammonium citrate dibasic, Ammonium formate, Ammonium oxalate monohydrate, Ammonium phosphate dibasic, Ammonium phosphate monobasic, Ammonium sodium phosphate dibasic tetrahydrate, Ammonium sulfate solution, Ammonium tartrate dibasic, BES buffered saline, BES, BICINE, BIS-TRIS, Bicarbonate buffer solution, Boric acid, CAPS, CHES, Calcium acetate hydrate, Calcium carbonate, Calcium citrate tribasic tetrahydrate, Citrate Concentrated Solution, Citric acid, hydrous, Diethanolamine, EPPS, Ethylenediaminetetraacetic acid disodium salt dihydrate, Formic acid solution, Gly-Gly-Gly, Gly-Gly, Glycine, HEPES, Imidazole, Lipoprotein Refolding Buffer, Lithium acetate dihydrate, Lithium citrate tribasic tetrahydrate, MES hydrate, MES monohydrate, MES solution, MOPS, Magnesium acetate solution, Magnesium acetate tetrahydrate, Magnesium citrate tribasic nonahydrate, Magnesium formate solution, Magnesium phosphate dibasic trihydrate, Oxalic acid dihydrate, PIPES, Phosphate buffered saline, piperazine, Potassium D-tartrate monobasic, Potassium acetate, Potassium bicarbonate, Potassium carbonate, Potassium chloride, Potassium citrate monobasic, Potassium citrate tribasic solution, Potassium formate, potassium hydroxide, Potassium oxalate monohydrate, Potassium phosphate dibasic, Potassium phosphate dibasic, for molecular biology, anhydrous, Potassium phosphate monobasic, Potassium phosphate monobasic, Potassium phosphate tribasic monohydrate, Potassium phthalate monobasic, Potassium sodium tartrate, Potassium sodium tartrate tetrahydrate, Potassium tetraborate tetrahydrate, Potassium tetraoxalate dihydrate, Propionic acid, STE buffer, STET buffer, Sodium 5,5-diethylbarbiturate, Sodium acetate, Sodium acetate trihydrate, Sodium bicarbonate, Sodium bitartrate monohydrate, Sodium carbonate decahydrate, Sodium carbonate, Sodium citrate monobasic, Sodium citrate tribasic dihydrate, Sodium formate solution, Sodium oxalate, Sodium phosphate dibasic dihydrate, Sodium phosphate dibasic dodecahydrate, Sodium phosphate dibasic solution, Sodium phosphate monobasic dihydrate, Sodium phosphate monobasic monohydrate, Sodium phosphate monobasic solution, Sodium pyrophosphate dibasic, Sodium pyrophosphate tetrabasic decahydrate, Sodium tartrate dibasic dihydrate, Sodium tartrate dibasic solution, Sodium tetraborate decahydrate, TAPS, TES, TM buffer solution, TNT buffer solution, TRIS Glycine buffer, TRIS acetate-EDTA buffer solution, TRIS buffered saline, TRIS glycine SDS buffer solution, TRIS phosphate-EDTA buffer solution, Tricine, Triethanolamine, Triethylamine, Triethylammonium acetate buffer, Triethylammonium phosphate solution, Trimethylammonium acetate solution, Trimethylammonium phosphate solution, Tris-EDTA buffer solution, Trizma® acetate, Trizma® base, Trizma® carbonate, Trizma® hydrochloride, Trizma® maleate, and combinations thereof.

Topical Formulations

The compositions of the invention may be, for example, administered topically. The compositions of the invention may be, for example, mixed with pharmaceutically suitable auxiliaries, e.g., as described in the standard reference, Gennaro et al., Remington: The Science and Practice of Pharmacy. 20$^{th}$ Edition Baltimore:Lippincott Williams & Wilkins, 2000. By means of pharmaceutically suitable liquids the compositions may be applied in the form of, for example, a solution, suspension, gel or emulsion. The compositions may also be formulated in, for example, a patch, ointment or can be enclosed in a device for local administration to the skin.

The term "topical" as employed herein relates to the use of a compound, derivative or analogue as described herein, incorporated in a suitable pharmaceutical carrier, and applied at the site of, for example, a wart, for exertion of local action. Accordingly, such topical compositions including those forms in which the composition is applied externally by direct contact with the skin surface to be treated. Conventional forms for this purpose include ointments, liniments, creams, shampoos, lotions, pastes, gels, sprays, aerosols, soaps, and the like, and may be applied in patches or impregnated dressings depending on the part of the body to be treated. The term "ointment" embraces formulations (including creams) having oleaginous, absorption, water-soluble and emulsion-type bases, e.g., petrolatum, lanolin, polyethylene glycols, as well as mixtures of these.

For topical use on the skin, eyelids, eyebrows, the compositions of the invention can be formulated in aqueous solutions, gels, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid, etc., as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. Depending on the actual formulation and the compositions of the invention to be used, various amounts of the drug and different dose regimens may be employed.

For topical use, the compositions of the invention can be advantageously formulated using ointments, gels, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. The compositions of the invention may be administered once or several times daily, with or without antioxidants.

Non-limiting examples of topical products can include, without limitation, application stick, mascara, eyebrow coloring products, eye shadow or other eye lid coloring products, eyeliner, make-up removal products, antiaging products, facial or body powder, nail polish, mousse, sprays, styling gels, nail conditioner, bath and shower gels, shampoos, conditioners, cream rinses, skin conditioners, sun tanning lotions and creams and sprays, sunscreens and sunblocks, skin conditioners, cold creams, moisturizers, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, and rinses.

Furthermore, the topical product can be applied topically, either in unit-dose or multi-use package, through the use of a patch or other applicator or delivery device. Delivery devices can include, but are not limited to, those that can be heated or cooled, as well as those that utilize iontophoresis or ultrasound.

For instance, the topical composition can be applied, for example, by applying a composition in the form of a skin lotion, clear lotion, milky lotion, cream, gel, foam, ointment, paste, emulsion, spray, conditioner, tonic, cosmetic, application stick, pencil, foundation, nail polish, after-shave, or the like which is intended to be left on the skin or other keratinous tissue (i.e., a "leave-on" composition). After applying the composition to the keratinous tissue (e.g., skin), it in one embodiment, it is left on for a period of at least about 15 minutes, or at least about 30 minutes, or at least about 1 hour, or for at least several hours, e.g., up to about 12 hours. In one embodiment, the topical product is left on overnight. In another embodiment, the topical product is left on all day. Any part of the external portion of the body can be treated, (e.g., face, lips, under-eye area, eyelids, scalp, neck, torso, arms, legs, chest, hands, legs, feet, toenails, scalp, eyelashes, eyebrows, etc.)

Any suitable method can be used to apply the topical product, including but not limited to for example using the palms of the hands and/or fingers or a device or implement (e.g., a cotton ball, swab, pad, applicator pen, spray applicator, eyebrow brush, eyebrow brush pencil, pencil, mascara brush, etc.) Another approach to ensure a continuous exposure of the keratinous tissue to at least a minimum level of the topical product is to apply the compound by use of a patch applied, e.g., to the face. The patch can be occlusive, semi-occlusive or non-occlusive, and can be adhesive or non-adhesive. The topical product can be contained within the patch or be applied to the skin prior to application of the patch. The patch can also include additional actives such as chemical initiators for exothermic reactions such as those described in PCT application WO 9701313, and in U.S. Pat. Nos. 5,821,250, 5,981,547, and 5,972,957 to Wu, et al. The patch can be left on the area to be treated for any suitable period of time. For example, a period of at least about 5 minutes, or at least about 15 minutes, or at least about 30 minutes, or at least about 1 hour, or at night as a form of night therapy, or in another embodiment all day.

The topical product can comprise any suitable desired materials. For instance, such materials can be selected from the group consisting of sugar amines (e.g., N-acetylglucosamine), vitamin B3 compounds, sodium dehydroacetate, dehydroacetic acid and its salts, phytosterols, soy derivaties (e.g., equol and other isoflavones), niacinamide, phytantriol, farnesol, bisabolol, salicylic acid compositions, hexamidines, dialkanoyl hydroxyproline compositions, flavonoids, N-acyl amino acid compositions, retinoids (e.g., retinyl propionate), water-soluble vitamins, ascorbates (e.g., vitamin C, ascorbic acid, ascorbyl glucoside, ascorbyl palmitate, magnesium ascorbyl phosphate, sodium ascorbyl phosphate), particulate materials, sunscreen actives, anti-cellulite agents, butylated hydroxytoluene, butylated hydroxyanisole, their derivatives, and combinations thereof. Other examples include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, surfactants, nonionic cosurfactants, pediculocides, pH adjusting agents, perfumes, preservatives, chelants, chelating agents, proteins, UV absorbers, pigments, other amino acids, and other vitamins.

For instance, topical products for use herein may comprise one or more vitamins and/or amino acids such as: water soluble vitamins such as vitamin B1, B2, B6, B12, C, pantothenic acid, pantothenyl ethyl ether, panthenol, biotin, and their derivatives, water soluble amino acids such as asparagine, alanine, indole, glutamic acid and their salts, water insoluble vitamins such as vitamin A, D, E, and their derivatives, water insoluble amino acids such as tyrosine, tryptamine, and their salts.

Topical products may also contain one or more pigment materials such as inorganic, nitroso, monoazo, diazo, carotenoid, triphenyl methane, triaryl methane, xanthene, quinoline, oxazine, azine, anthraquinone, indigoid, thionindigoid, quinacridone, phthalocianine, botanical, natural colors, including water soluble components. The topical products may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

In some embodiments, the composition is chronically applied to the skin. By "chronic topical application" is meant continued topical application of the composition over an extended period during the subject's lifetime, for example, for a period of at least about one week, or for a period of at least about one month, or for at least about three months, or for at least about six months, or for at least about one year. While benefits are obtainable after various periods of use (e.g., five, ten or twenty years), chronic application can continue throughout the subject's lifetime. Typically applications would be on the order of about once per day over such extended periods, however application rates can vary from about once per week up to about three times per day or more.

Regulating keratinous tissue condition can be practiced by applying a composition of the invention in the form of a skin lotion, cream, gel, foam, ointment, paste, emulsion, spray, conditioner, tonic, cosmetic, lipstick, foundation, nail polish, after-shave, or the like that is preferably intended to be left on the skin or other keratin structure for some esthetic, prophylactic, therapeutic or other benefit (i.e., a "leave-on" composition). After applying the composition to the skin, it can be left on the skin for a period of at least about 15 minutes, or at least about 30 minutes, or at least about 1 hour, or for at least several hours, for example, up to about 12 hours.

Additional Ingredients

In addition, the compositions of the invention may include various other and additional ingredients, which may be active, functional, conventionally used in cosmetic, personal care or topical/transdermal pharmaceutical products or otherwise. Of course, a decision to include an additional ingredient and the choice of specific additional ingredients depends on the specific application and product formulation. Also, the line of demarcation between an "active" ingredient and an "inactive ingredient" is artificial and dependent on the specific application and product type. A substance that is an "active" ingredient in one application or product may be a "functional" ingredient in another, and vice versa. A particular ingredient might provide substantivity in one formulation, facilitate transdermal application in another, and merely provide proper viscosity in a third. Which of these is functional and which is active is subject to debate. But, regardless of the outcome, the material in question would qualify as an additional ingredient in accordance with the present invention.

Thus, the compositions of the invention may include one or more additional ingredients, which provide some benefit to the object of the composition. Such additional ingredients may include one or more substances such as, without limitations, cleaning agents, conditioning agents, skin conditioning agents, antidandruff agents, growth promoters, perfumes, sunscreen and/or sunblock compositions, pigments, moisturizers, film formers, colors, make-up agents, detergents, pharmaceuticals, thickening agents, emulsifiers, humectants, emollients, antiseptic agents, deodorant actives, dermatologically acceptable carriers, surfactants, bleaching agents, and combinations thereof.

The compositions of the present invention generally contain at least one additional ingredient. The compositions of the present invention may contain a plurality of additional ingredients as well.

The CTFA Cosmetic Ingredient Handbook, Ninth Edition (2002) describes a wide variety of nonlimiting cosmetic and pharmaceutical ingredients commonly used in the skin care industry, which are suitable for use as additional ingredients in the compositions of the present invention. Non-limiting examples of these additional ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, vitamins and derivatives thereof, bleaching agents, and combinations thereof.

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

The invention will be illustrated in more detail with reference to the following Examples, but it should be understood that the present invention is not deemed to be limited thereto.

EXAMPLES

Example 1

The inventors have developed the following exemplary formulation, designated as CLS003. The CLS003 drug product is a topical gel containing both digoxin and furosemide each at concentrations of 0.125% w/w. The quantitative formulation is provided below:

CLS003

| | |
|---|---|
| Dehydrated Alcohol (Ethanol) 200 proof, USP | 38.7% |
| Digoxin, Ph.Eur/USP | 0.125% |
| Furosemide, Ph.Eur/USP | 0.125% |

-continued

| | |
|---|---|
| Propylene Glycol, USP | 48.375%* |
| 100 mM Citrate Buffer, pH5.5**, pH. EUR/USP | 9.675% |
| Hydroxypropyl Cellulose, Ph. EUR/USP | 3.00% |

*For gels containing either digoxin or furosemide alone, propylene glycol may be increased.
**100 mM citrate buffer, pH 5.5 consists of:
~320 parts of a solution containing 19.21 g Citric Acid Anhydrous Ph. EUR/USP/1000 mL Purified Water Ph. EUR/USP
~680 parts of a solution containing 29.40 g Sodium Citrate Dihydrate. Ph. EUR/USP/1000 mL Purified Water Ph. EUR/USP Example 2

The Inventors conducted a study regarding digoxin, furosemide, and digoxin-furosemide combination topical formulations. The study tested the effects of single and combined drugs on virus DNA and RNA replication. Bio-banked HPV-positive Hela S3 cells were cultured and then incubated for 24 hours with varying concentrations of digoxin, furosemide, and digoxin-furosemide combination. Quantitative PCR was used to determine the anti-viral activity of the compounds. Digoxin showed a dose-dependent anti-viral activity both on HPV DNA (viral load) and mRNA levels. Furosemide treatment at the highest dose showed anti-viral effect on HPV viral load and mRNA levels. Cidofovir, another known antiviral drug for DNA virus, effectively inhibited HPV mRNA but not the viral load at 24 hours. Combined digoxin-furosemide drug treatments showed significant decreases on the HPV viral load and mRNA levels. Hela cells were treated with a different combination of digoxin (0, 0.5, 2 µg/mL) and furosemide (50, 100, 200, 500 µg/mL). As experimental controls, non-drug treated and cidofovir (65 µM) treated wells were also included. Combined drug treatments showed synergistic effects on anti-viral activity.

Specifically, among all drug combinations tested, the most effective anti-viral effect on viral DNA was digoxin at 2 µg/mL in the presence of furosemide at 200 or 500 µg/mL. The data are summarized in Table 1.

TABLE 1

Summary of In vitro efficacy against HPV18 in Hela cell culture. Single and combined drug 24 hour treatment experiment (10-1 to 10-3 2012) $^a$

| Digoxin (µg/mL) | Furosemide (µg/mL) | HPV DNA (pg) | HPV RNA 2 (-ΔΔCT) = RQ | HPV RNA Log10RQ |
|---|---|---|---|---|
| Controls (no drug or cidofovir) | | | | |
| 0 | 0 | 27.34 | 1.000 | 0.00 |
| Cidofovir | | 17.38 | 0.119 | −0.92 |
| Furosemide alone | | | | |
| 0 | 50 | 26.87 | 1.268 | 0.10 |
| 0 | 100 | 11.62 | 1.305 | 0.12 |
| 0 | 200 | 26.64 | 1.127 | 0.05 |
| 0 | 500 | 10.51 | 1.321 | 0.12 |
| Digoxin and furosemide in combination | | | | |
| 0.5 | 50 | 17.72 | 0.219 | −0.66 |
| 0.5 | 100 | 10.10 | 0.281 | −0.55 |
| 0.5 | 200 | 17.59 | 0.341 | −0.47 |
| 0.5 | 500 | 13.32 | 0.321 | −0.49 |
| 2 | 50 | 12.74 | 0.075 | −1.13 |
| 2 | 100 | 15.83 | 0.055 | −1.26 |
| 2 | 200 | 11.86 | 0.051 | −1.29 |
| 2 | 500 | 7.12 | 0.107 | −0.97 |

Figure 2:
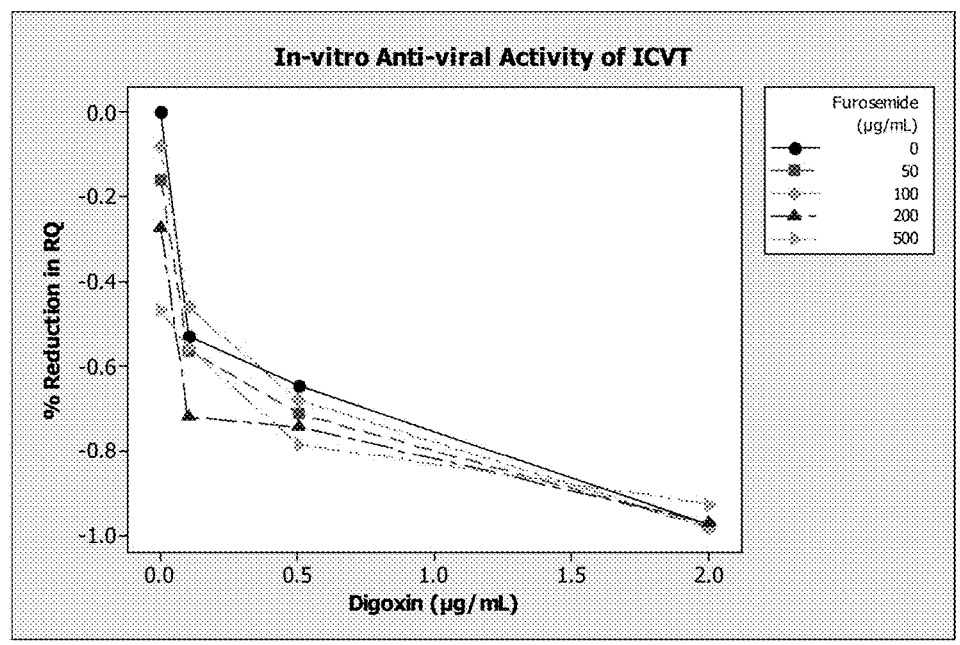
FIG. 2 shows the In-vitro anti-viral activity of Ionic Contra-Viral Therapy; Summary of in vitro efficacy against HPV18 in Hela cell culture; % Reduction in Relative Quantification. Single and combined drug 48 hour treatment experiment.

The inventors further conducted an in vitro study to test the efficacy of digoxin and furosemide through the examination of viral load. Hela S3 cells were treated with different combinations of digoxin (0, 0.1, 0.5, 2 µg/mL) and furosemide (0, 50, 100, 200, 500 µg/mL). Non-drug treated (NT) cells and cidofovir (65 µM) treated cells served as controls. The study took place over a total of four days. Anti-viral effects were clearly observed at the 48-hour mark in the treated sample. A clear dose-dependent anti-viral activity on DNA viral load, as well as anti-viral activity indicated by mRNA, was observed in both furosemide- and digoxin-treated samples, as consistent with the previous results. Again, furosemide effects were observed most significantly in the presence of 2 µg/mL of digoxin for both DNA viral load and mRNA-indicated anti-viral activity. Cidofovir inhibited HPV mRNA; it did not have an effect on DNA viral load at 24 hours, but did affect the viral load at 48 hours. The data are summarized in the Table 2 and FIGS. 1 and 2.

TABLE 2

Summary of in vitro efficacy against HPV18 in Hela cell culture. Single and combined drug 48 hour treatment experiment (11-26 to 11-30 2012) $^a$

| Digoxin (µg/mL) | Furosemide (µg/mL) | HPV DNA (pg) | HPV RNA 2 (-ΔΔCT) = RQ | HPV RNA Log10RQ |
|---|---|---|---|---|
| Controls (no drug or cidofovir) | | | | |
| 0 | 0 | 33.87 | 1.000 | 0.00 |
| Cidofovir | | 21.30 | 0.053 | −1.27 |
| 0.1 | 0 | 21.80 | 0.471 | −0.33 |
| 0.5 | 0 | 10.16 | 0.353 | −0.45 |
| 2 | 0 | 3.93 | 0.026 | −1.58 |
| 0 | 50 | 29.67 | 0.837 | −0.08 |
| 0 | 100 | 43.45 | 0.918 | −0.04 |
| 0 | 200 | 25.94 | 0.725 | −0.14 |
| 0 | 500 | 21.30 | 0.531 | −0.27 |
| Digoxin and furosemide in combination | | | | |
| 0.1 | 50 | 20.38 | 0.437 | −.036 |
| 0.1 | 100 | 14.85 | 0.539 | −0.27 |
| 0.1 | 200 | 14.07 | 0.279 | −0.55 |
| 0.1 | 500 | 7.91 | 0.444 | −0.35 |
| 0.5 | 50 | 9.59 | 0.289 | −0.54 |
| 0.5 | 100 | 10.27 | 0.321 | −0.49 |
| 0.5 | 200 | 6.00 | 0.257 | −0.59 |
| 0.5 | 500 | 4.90 | 0.215 | −0.67 |
| 2 | 50 | 3.21 | 0.020 | −1.7 |
| 2 | 100 | 3.41 | 0.018 | −1.74 |
| 2 | 200 | 3.73 | 0.029 | −1.54 |
| 2 | 500 | 3.77 | 0.073 | −1.14 |

Example 3

The inventors further conducted a stability study comparing non-buffered and buffered formulations. The Tables below summarizes the improved stability profile of the buffered formulation as compared to a non-buffered formulation. These are 6 month stressed storage results. In the presence of the buffer, the active potency is maintained, and the number and level of degradation products is significantly reduced. The non-buffered formulation is not commercially viable due to the formulation; whereas, the buffered formulation represents a commercially viable product.

| Test Parameter | Non-buffered Topical Gel | | Citrate-buffered Topical Gel | |
| --- | --- | --- | --- | --- |
| | T0 | T6M 40° C./75% RH | T0 | T6M 40° C./75% RH |
| Assay-DIG (% LC) | 97.4% | 79.7% | 98.6% | 100.5% |
| Degradation products Digoxin (% LC) | 0.41% (RRT 0.84) Total = 0.41% | 4.26% (RRT 0.41) 3.12% (RRT 0.60) 8.10% (RRT 0.84) Total = 15.48% | 0.46% (RRT 0.84) Total = 0.46% | 0.62% (RRT 0.84) Total = 0.62% |
| Assay-FSM (% LC) | 97.2% | 84.6% | 99.9% | 103.0% |
| Degradation products Furosemide (% LC) | 0.05% (RRT 0.18) Total = 0.05% | 2.79% (RRT 0.16) 5.49% (RRT 0.18) 0.09% (RRT 0.26) 0.07% (RRT 0.60) 0.14% (RRT 0.71) 0.49% (RRT 0.91) 0.07% (RRT 1.35) Total = 9.14% | Total = BLQ | 0.13% (RRT 0.16) 0.13% (RRT 0.18) Total = 0.26% |

Example 4

Two in vitro studies compared the percutaneous absorption delivery of both digoxin and furosemide to receptor fluid using a Franz-cell diffusion chamber between the citrate buffered formulation, which includes digoxin 0.125%/furosemide 0.125% with citrate buffer, along with the unbuffered formulation. The studies measured the flux of both furosemide and digoxin, and the compound accumulation of both digoxin and furosemide in the dermis and epidermis skin sections. The results of human cadaver skin studies are summarized in Table 3 and Table 4.

TABLE 3

Percutaneous Absorption of Digoxin in Human Cadaver Skin

| Human Cadaver Skin Study† | Parameter | Unbuffered Formulation | Citrate Buffered Formulation |
| --- | --- | --- | --- |
| Study 1 | Flux (pmol/cm²/h) | 0.15 ± 0.13 | 1.88 ± 0.85 |
| | Accumulation in epidermis (µg/g) | 12.6 ± 5.00 | 11.2 ± 1.02 |
| | Accumulation in dermis (µg/g) | 4.50 ± 0.22 | 4.56 ± 4.19 |
| Study 2 | Flux (pmol/cm²/h) | 0.30 ± 0.22 | 1.96 ± 1.31 |
| | Accumulation in epidermis (µg/g) | 24.8 ± 10.5 | 12.9 ± 6.07 |
| | Accumulation in dermis (µg/g) | 2.75 ± 1.05 | 4.19 ± 4.16 |

TABLE 4

Percutaneous Absorption of Furosemide in Human Cadaver Skin

| Human Cadaver Skin Study | Parameter | Unbuffered Formulation | Citrate Buffered Formulation |
| --- | --- | --- | --- |
| Study 1 | Flux (pmol/cm²/h) | 29.40 ± 8.90 | 16.4 ± 1.76 |
| | Accumulation in epidermis (µg/g) | 78.2 ± 19.7 | 44.4 ± 9.66 |
| | Accumulation in dermis (µg/g) | 4.98 ± 1.00 | 3.51 ± 1.87 |
| Study 2 | Flux (pmol/cm²/h) | 21.8 ± 5.89 | 52.2 ± 26.9 |
| | Accumulation in epidermis (µg/g) | 142 ± 15.7 | 121 ± 15.1 |
| | Accumulation in dermis (µg/g) | 2.74 ± 0.91 | 5.37 ± 5.26 |

Summary of Results

The Citrate Buffered Formulation consistently exhibited a trend of higher permeation of both digoxin and furosemide than the Unbuffered Formulation across the human skin specimen used in the current study.

The overall flux data from Citrate Buffered Formulation was more linear than that from Unbuffered Formulation.

For both digoxin and furosemide, Unbuffered Formulation appeared to result in higher accumulation in epidermis than Citrate Buffered Formulation.

For both digoxin and furosemide, Citrate Buffered Formulation appeared to result in higher accumulation in dermis than Unbuffered Formulation.

The formulation of the invention have the further benefit of limiting systemic exposure. While the flux (J) of digoxin in the buffered formulation is improved over that of the unbuffered, the digoxin levels are still well within the margin of safety established in the non-clinical mini-pig model.

The results for digoxin plasma concentrations observed in the completed 7-day minipig study formed the basis for justification of the human dose. The data from the group treated with the 0.125% w/w digoxin 0.125% w/w furosemide formulation were most relevant as this is the formulation for clinical study. In the minipig study the treated area was 270 cm² representing 10% of body surface area (BSA) and the standard dose applied was 2.6 mL. The resulting mean±SD day 7 $C_{max}$ was 1,045±1,065 pg/mL (1.045±1.065 ng/mL). This provides an estimate of the 95% confidence interval upper limit of 3,132 pg/mL (3.132 ng/mL) for the day 7 $C_{max}$.

A reasonable limitation was considered to be 10-fold below the application area in the 7-day minipig study, or 1% of BSA not to exceed 7 days of application. If the digoxin bioavailability was the same in man as in mini pigs, a conservative estimate of the mean day 7 $C_{max}$ was approximately 300 pg/mL (0.30 ng/mL). Human body surface area is 18,000 cm² and 16,000 cm² for males and females, respectively. The maximum application area should be limited to 160 cm² and the maximum dose volume should be limited to 1.6 mL of the gel per day (approximately 1,500 mg). For additional information please refer to the Investigator's Brochure.

Based upon literature and preclinical data a PK simulation of digoxin was also established. The following assumptions were made:
i) (pseudo) zero order release from formulation, i.e upper layers of stratum corneum through skin barrier;
ii) Flux input during 7 consecutive days;

iii) Flux (J=31 pmol/cm²/h); derived from ex vivo experiment (CLS003 on human cadaver skin);
iv) KR=0.33 h⁻¹ (compound specific release rate constant) was estimated from literature [6];
v) Simplified 1 compartmental model (absorption of transdermal digoxin into central plasma compartment);
vi) Skin reservoir depletes in <56 h after last administration;
vii) Systemic PK parameters: Vd=548 L; Cl=9.5 L/h; (based on Dutch National Formulary);
viii) Surface (S)=98 cm²; and
ix) Conservative estimation where no degradation in skin compartment takes place.

The simulation of the PK of digoxin with these assumptions lead to a $C_{max}$ in plasma of 0.235 ng/mL, which is more than three times below the minimal effective dose for indications heart failure and atrium fibrillation and 8.5 times lower than the minimal toxic dose.

Example 5

In addition, the formulation of the invention exhibits improved stability over previous formulations.
  12 Month stressed condition stability on citrate-buffered dual gel (digoxin and furosemide)
  6 Month stressed condition stability data on a phosphate buffered gel which also demonstrate acceptable stability over a different pH range; however, the digoxin-related impurity profile was not as satisfactory as that of citrate buffer at the same stability time point (as shown in the patent application p. 25.)
  6 Month stressed condition stability data on NaOH-containing gel, adjusted to pH 6.7.
  6 Month stressed condition stability on the individual, digoxin-only, citrate-buffered gel formulation

| Formulation | Storage Condition | Assay | Level of impurities | pH range |
|---|---|---|---|---|
| Citrate-buffered dual gel (digoxin + furosemide)/ | 12M 40° C./ 75% RH | DIG: 98.8% (t0 = 98.6%) FSM: 100.6% (t0 = 99.9%) | DIG-related: 0.97% FSM-related: 0.48% | 6.5-6.8 |
| Phosphate-buffered dual gel (digoxin + furosemide)/ | 6M 40° C./ 75% RH | DIG: 98.5% (t0 = 101.0%) FSM: 100.7% (t0 = 101.8%) | DIG-related: 2.82% FSM-related: 0.16% | 5.3-5.8 |
| NaOH pH adjusted dual gel (digoxin + furosemide)/ | 6M 40° C./ 75% RH | DIG: 100.1% (t0 = 99.4%) FSM: 103.1% (t0 = 102.6%) | DIG-related: 0.72% FSM-related: 0.17% | 6.5-6.8 |
| Citrate-buffered digoxin-only gel | 6M 40° C./ 75% RH | DIG: 95.1% (t0 = 97.0%) | 0.52% (t0 = 0.44%) | 6.7-6.8 |

Example 6

The formulation of the invention exhibits improved stability over previous formulations, even in stressed conditions.

Quantitative composition of 0.125% w/w Furosemide Topical Gel (Formulation No. 3672)

| Component | % w/w |
|---|---|
| Furosemide | 0.125 |
| Ethanol | 38.75 |
| Propylene Glycol | 48.4375 |
| Hydroxypropyl Cellulose | 3.00 |
| 100 mM Citrate Buffer | 9.6875 |

Stability Data for Furosemide Single Active 0.125% (w/w) Furosemide Citrate Buffered Gel (FID#3672) in Glaminate tubes Lot: CTA974_001-02 (R&D)
Storage at 25 C/60% RH

| Time point (Month) | 0 | 3 | 6 |
|---|---|---|---|
| pH | 6.5 | 6.4 | NT |
| Assay (% LC) | 101.2% | 102.3% | 101.4% |
| Sum of Related substances (% LC) | 0.19% | 0.17% | 0.25% |

Storage at 40 C/75% RH

| Time point (Month) | 0 | 3 | 6 |
|---|---|---|---|
| pH | 6.5 | 6.5 | NT |
| Assay (% LC) | 101.2% | 101.2% | 102.1% |
| Sum of Related substances (% LC) | 0.19% | 0.24% | 0.28% |

0.125% (w/w) Furosemide Citrate Buffered Gel (FID#3672) in Glaminate tubes Lot: 36720110914 (GMP)
Storage at 25 C/60% RH

| Time point (Month) | 0 | 6 |
|---|---|---|
| pH | 6.7 | 6.8 |
| Assay (% LC) | 96.5% | 100.8% |
| Sum of Related substances (% LC) | 0.13% | 0.13% |

Storage at 40 C/75% RH

| Time point (Month) | 0 | 6 |
|---|---|---|
| pH | 6.7 | 6.9 |
| Assay (% LC) | 96.5% | 100.7% |
| Sum of Related substances (% LC) | 0.13% | 0.16% |

Example 7

The Inventors conducted an Ionic Contra Viral Therapy Phase 2 Study. The study tested the effects of topical application of the compositions of the invention comprising furosemide alone, digoxin alone, or digoxin-furosemide combination as compared to control vehicle only. The compositions were tested against Common and plantar warts in test subjects. No effect or activity of vehicle was observed. Clearance and reduction of untreated warts occurs in active treatment groups (not with vehicle).

Efficacy Results

All three active treatments showed statistical significant effects on wart size reduction in all treated warts compared to vehicle, with the most pronounced effect of the dual active, i.e. digoxin+furosemide. Similar effects of the three active treatments were observed on wart clearance while vehicle treatment did not result in completely cleared lesions. In addition, qPCR data showed an effect on viral load reduction of any HPV in swabs with CLS003 in all treatment groups compared to vehicle.

Safety Results

The results from the current study show that CLS003 is safe and well tolerated with once-daily (QD) administration for up to 42 consecutive days to subjects with cutaneous warts. The overall incidence of Treatment-Emergent Adverse Events (TEAEs) was similar among subjects receiving active treatment and vehicle. No clinically significant changes were attributable to treatment with CLS003 for any haematology, clinical chemistry, urinalysis, vital signs, or electrocardiographic (ECG) parameters.

The following Table presents a Summary of the clearance of both treated and untreated warts in active treatment groups (not with vehicle) for both common and plantar warts.

As can be seen, clearance is approximately double for common over plantar, as shown in the following Table.

TABLE 5

| Treatment | Wart Type | Number treated and untreated | Cleared n (%) |
|---|---|---|---|
| Vehicle | Common | 32 | 0 (0%) |
|  | Plantar | 27 | 0 (0%) |
| Dig + Fur | Common | 19 | 4 (21.0%) |
|  | Plantar | 26 | 3 (11.5%) |
| Digoxin | Common | 30 | 7 (23.3%) |
|  | Plantar | 23 | 2 (8.7%) |
| Furosemide | Common | 31 | 7 (22.6%) |
|  | Plantar | 30 | 4 (13.3%) |

Figure 3:
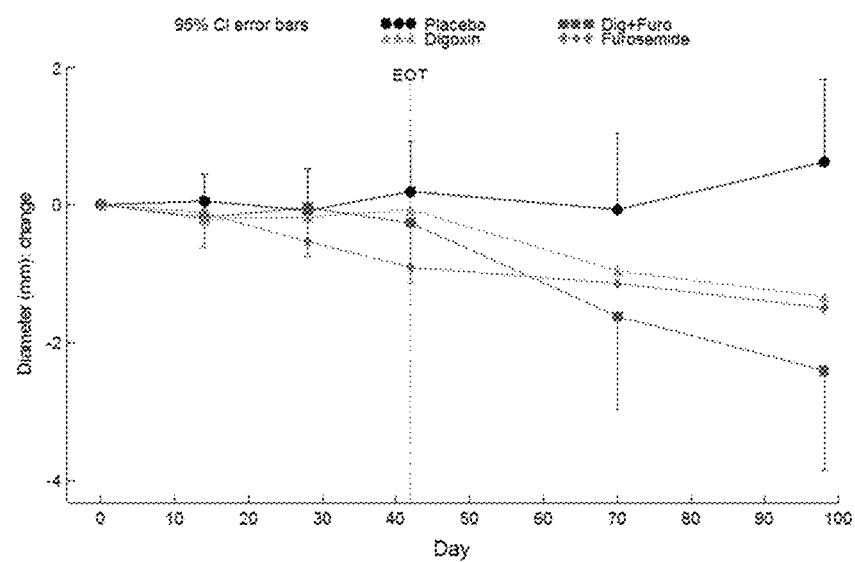
FIG. 3 shows the Pharmacodynamics of All Treated Warts ITT least squares means (LSM) Diameter.
Figure 4:
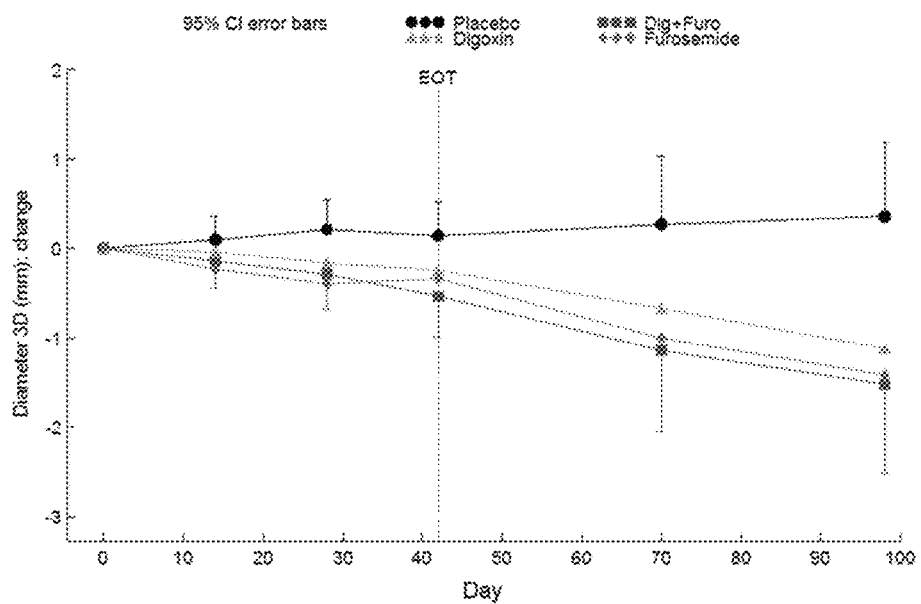
FIG. 4 shows the Pharmacodynamics of All Treated Warts ITT least squares means (LSM) Diameter (3D).
Figure 5:
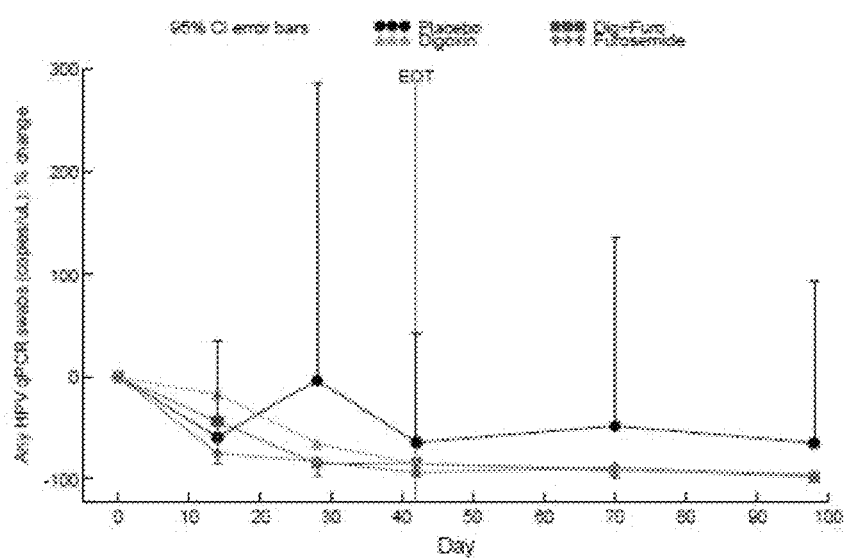
FIG. 5 shows the least squares means (LSM) change from baseline graph of any HPV in swabs from primary warts (% change) with 95% CI as error bars.

The data is presented in FIGS. 3 and 4. The data for the Pharmacodynamics of All Treated Wart Clearance is summarized in the following Table:

TABLE 6

| Treatment | Not Clear | Clear |
|---|---|---|
| Vehicle | 38 (100%) | 0 (0%) |
| Dig + Fur | 21 (81%) | 5 (19%) |
| Digoxin | 26 (81%) | 6 (19%) |
| Furosemide | 33 (80%) | 8 (20%) |

While the invention has been described in detail and with reference to specific examples thereof, it will be apparent to one skilled in the art that various changes and modifications can be made therein without departing from the spirit and scope thereof.

What is claimed is:

1. A pharmaceutical topical gel formulation comprising:
   about 0.125% digoxin;
   alkylene glycol in the range of about 20-60% w/w;
   ethanol in the range of about 20-60% w/w;
   at least one thickener in the range of about 0.5% to 5% w/w;
   a buffer which maintains the formulation pH at about pH 3 to about pH 8, wherein the buffer is citric acid and sodium citrate; and
   optionally, polyalkylene glycol in the range of about 0-20% w/w;
   q.s. with water,
   wherein the concentrations are based on the total weight of the formulation, further wherein the topical gel formulation is anti-viral.

2. A pharmaceutical topical gel formulation as claimed in claim 1, wherein the topical gel formulation is storage stable at room temperature.

3. A pharmaceutical topical gel formulation as claimed in claim 1, wherein the topical gel formulation is capable of cutaneous and/or dermal delivery.

4. A pharmaceutical topical gel formulation as claimed in claim 1, in which the thickener comprises one or more of the following: Carbomers, cellulose derivatives, or hydroxyalkylcellulose.

5. A pharmaceutical topical gel formulation as claimed in claim 1, wherein the thickener comprises hydroxypropylcellulose, in an amount of about 1 to 5% by weight based on the total weight of the formulation.

6. A pharmaceutical topical gel formulation as claimed in claim 1, for use in the treatment of DNA viral infections selected from viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof.

7. A method for treating a disease or condition in a patient, wherein the disease or condition is selected from the group consisting of viral infections, human papilloma virus infection, latent HPV infection, sub-clinical HPV infection, clinical HPV infection, RNA viral infections, herpes simplex viral infections, actinic keratosis, Epidermodysplasia verruciformis, human T-lymphotropic virus type I (HTLV-1), EBV, CMV, SV40-like virus, hepatitis virus, human immunodeficiency virus (HIV), adenovirus, influenza virus, VIN (vulvar intraepithelial neoplasia), CIN (cervical intraepithelial neoplasia), and combinations thereof, wherein said method comprises:
   selecting a patient in need of treating said disease or condition;
   administering to the patient the pharmaceutical topical gel composition of claim 1 in a therapeutically effective amount,
   thereby treating said disease in said patient.

* * * * *